US010810180B1

(12) United States Patent
Saeed et al.

(10) Patent No.: US 10,810,180 B1
(45) Date of Patent: Oct. 20, 2020

(54) METHODS AND SYSTEMS FOR COMPRESSING DATA

(71) Applicants: Fahad Saeed, Miami, FL (US); Muhammad Haseeb, Miami, FL (US)

(72) Inventors: Fahad Saeed, Miami, FL (US); Muhammad Haseeb, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

(21) Appl. No.: 16/685,374

(22) Filed: Nov. 15, 2019

(51) Int. Cl.
  *G06F 16/22*  (2019.01)
  *G16B 50/30*  (2019.01)
  *G06F 16/25*  (2019.01)

(52) U.S. Cl.
  CPC ........ *G06F 16/2272* (2019.01); *G06F 16/258* (2019.01); *G16B 50/30* (2019.02)

(58) Field of Classification Search
  CPC .................................................. G06F 16/2272
  See application file for complete search history.

(56) References Cited

U.S. PATENT DOCUMENTS

| 6,502,064 B1* | 12/2002 | Miyahira | G06F 40/242 704/7 |
| 6,886,130 B1* | 4/2005 | Unger | G06F 16/957 715/207 |
| 2004/0044481 A1* | 3/2004 | Halpern | G16B 50/00 702/19 |
| 2008/0036630 A1* | 2/2008 | Lee | H03M 7/3084 341/51 |
| 2013/0191351 A1* | 7/2013 | Baym | G16B 50/00 707/693 |
| 2014/0108323 A1* | 4/2014 | Leighton | G16B 30/00 706/50 |
| 2016/0112722 A1* | 4/2016 | Rowny | H04N 9/04 348/231.2 |

* cited by examiner

*Primary Examiner* — Kris E Mackes
(74) *Attorney, Agent, or Firm* — Saliwanchik, Lloyd & Eisenschenk

(57) ABSTRACT

Methods and systems for compressing data, such as ion-mass information data in mass spectrometry spectra, to reduce index size are provided. Data in an index, such as fragment-ion data in a fragment-ion index, can be transformed for reduction of entropy and then encoded using a running counter technique to compress repetitive and redundant information in the index.

14 Claims, 3 Drawing Sheets

METHODS AND SYSTEMS FOR COMPRESSING DATA

GOVERNMENT SUPPORT STATEMENT

This invention was made with government support under Award number CRII CCF-1855441 and Award Number OAC-1925960, awarded by the National Science Foundation (NSF). The government has certain rights in the invention.

BACKGROUND

In a shotgun proteomics experiment, a complex protein mixture is proteolyzed using an enzyme and then fed to a pipeline of liquid-chromatography (LC) followed by mass spectrometry (MS/MS). The acquired tandem MS/MS spectra data, called experimental spectra, are identified using computational techniques, most commonly by using database search. Database search involves searching the experimental MS/MS spectra against a set of theoretical MS/MS spectra predicted from a protein sequence database. It has been shown that unrestricted peptide search methods allow larger peptide identification rates as compared to restricted search methods. However, unrestricted peptide search methods consume result in very large search times due to the massively increased number of required computationally expensive spectral comparisons. Therefore, most modern peptide search algorithms employ database filtration methods, most commonly peptide precursor mass, sequence-tagging and shared-peak counting to attempt to reduce the search space to only the relevant entries when searching an experimental spectrum. All such methods require huge memory read/write and caching overheads.

BRIEF SUMMARY

Embodiments of the subject invention provide methods and systems for compressing data (e.g., ion-mass information data in mass spectrometry spectra) to reduce index size. Embodiments reduce memory footprint during a search, such as the memory footprint of a fragment-ion index in a database peptide search for mass spectrometry data, as well as improve the scalability of algorithms. Data in an index (e.g., fragment-ion data in a fragment-ion index) can be transformed for reduction of entropy and then encoded using a running counter technique to compress repetitive and redundant information in the index.

In many embodiments, a custom data structure can be used specifically for indexing fragment-ion data (e.g., in a fragment-ion index). The data can be transformed to reduce its entropy and then encoded to pack the information into a much smaller amount of memory. The custom data structure does not require any decompression to search the index data and provides all the necessary functionality that existing uncompressed structures provide without any overhead. The data structure can be used on any database, including publicly available databases. Publicly available databases were used to evaluate the data structure against related art data structures, and the data structure of embodiments of the subject invention showed a 50%+ reduction in memory consumption, compared to related art data structures, while exhibiting the same speeds as the related art data structures. The data structure of embodiments of the subject invention also showed improved peptide inference speed performance over growing data size using a given amount of resources.

In an embodiment, a system for compressing data to reduce index size can comprise: a processor; and a (non-transitory) machine-readable medium (e.g., a (non-transitory) computer-readable medium) in operable communication with the processor and comprising instructions stored thereon that, when executed by the processor, perform the following steps: receiving an index comprising the data; transforming the data to reduce its entropy and give transformed data; and encoding the transformed data to reduce an amount of memory used by the transformed data and to give a custom data structure with reduced size compared to the received index. The custom data structure can be searchable without requiring any decompression prior to searching. The system can further comprise memory in operable communication with the processor and/or the machine-readable medium. The index can be a fragment-ion index, and the data can comprise mass spectrometry data (e.g., mass spectrometry data of one or more peptides). The encoding of the transformed data can comprise using a running counter technique to compress repetitive and redundant information in the transformed data.

In another embodiment, a method for compressing data to reduce index size can comprise: receiving an index comprising the data; transforming (e.g., by a processor) the data to reduce its entropy and give transformed data; and encoding (e.g., by the processor) the transformed data to reduce an amount of memory used by the transformed data and to give a custom data structure with reduced size compared to the received index. The custom data structure can be searchable without requiring any decompression prior to searching. The index can be a fragment-ion index, and the data can comprise mass spectrometry data (e.g., mass spectrometry data of one or more peptides). The encoding of the transformed data can comprise using a running counter technique to compress repetitive and redundant information in the transformed data.

DETAILED DESCRIPTION

Figure 1:
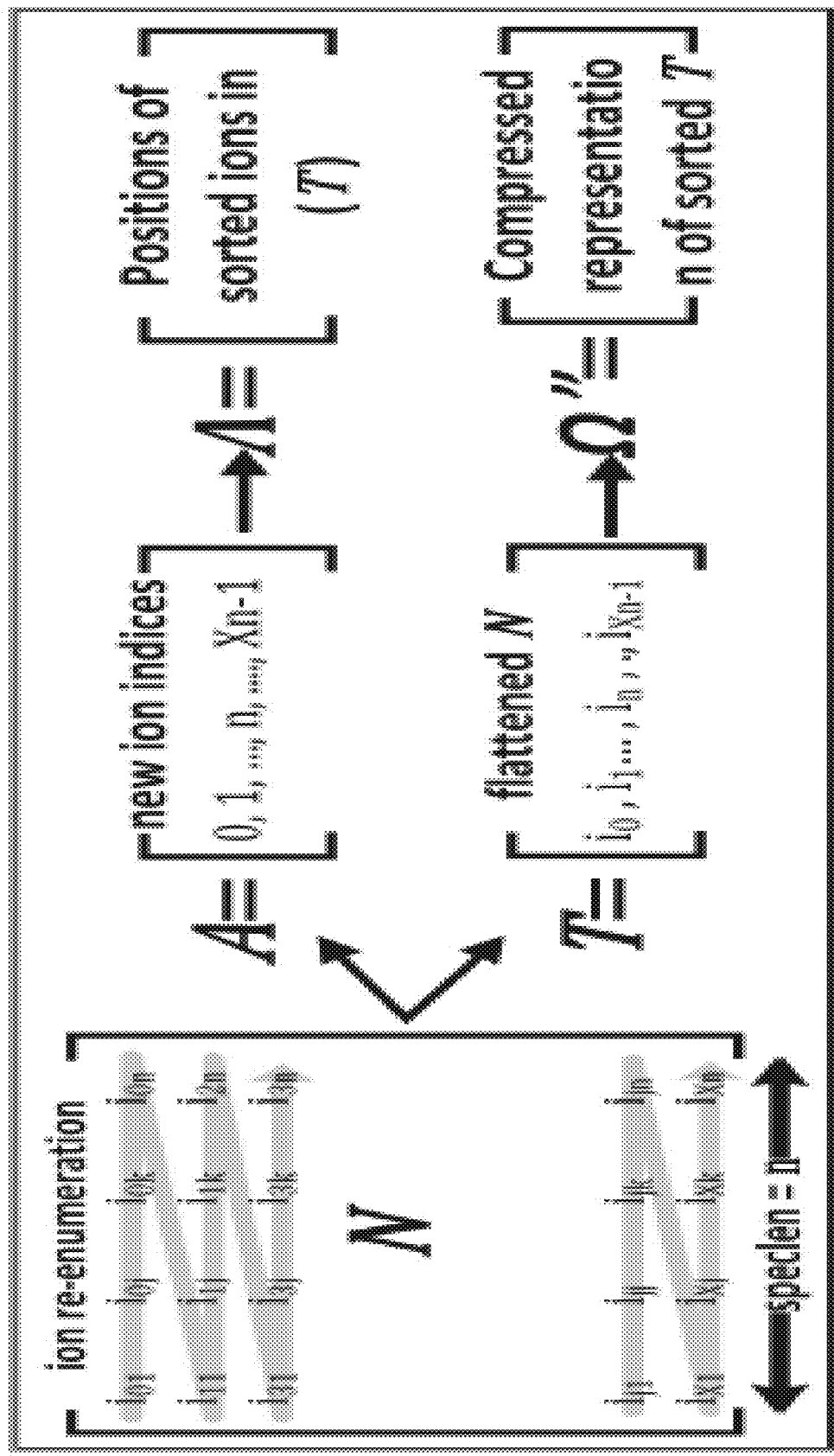
FIG. 1 is a schematic of data representation according to an embodiment of the subject invention.

Embodiments of the subject invention provide methods and systems for compressing data (e.g., ion-mass information data in mass spectrometry spectra) to reduce index size. Embodiments reduce memory footprint during a search, such as the memory footprint of a fragment-ion index in a database peptide search for mass spectrometry data, as well as improve the scalability of algorithms. Data in an index (e.g., fragment-ion data in a fragment-ion index) can be transformed for reduction of entropy and then encoded using a running counter technique to compress repetitive and redundant information in the index.

In many embodiments, a custom data structure can be used specifically for indexing fragment-ion data (e.g., in a fragment-ion index). The data can be transformed to reduce its entropy and then encoded to pack the information into a much smaller amount of memory. The custom data structure does not require any decompression to search the index data and provides all the necessary functionality that existing uncompressed structures provide without any overhead. The data structure can be used on any database, including publicly available databases. Publicly available databases were used to evaluate the data structure against related art data structures, and the data structure of embodiments of the subject invention showed a 50%+ reduction in memory consumption, compared to related art data structures, while exhibiting the same speeds as the related art data structures. The data structure of embodiments of the subject invention also showed improved peptide inference speed performance over growing data size using a given amount of resources.

Shared-peak count is employed by various modern peptide search algorithms in combination with several other similarity metrics for search space filtration and peptide deduction. Shared peak counting techniques typically construct an (inverted) fragment-ion index to speed up the computation at the cost of a substantially large memory footprint. The fragment-ion look up (search) from a large index, specifically using multiple cores, is accompanied by huge memory read/write and caching overheads in related art methods. Further, as the database size increases, the index spans over multiple non-unified memory access (NUMA) nodes, may be swapped several times (page faults), and/or may need to be split into smaller independent chunks and processed sequentially. Therefore, there is a need in the art to improve and/or optimize the fragment-ion index, compared to related art systems/structures/methods, without compromising the shared-peak counting speed.

Embodiments of the subject invention address this need by providing a compact data structure for fragment-ion data that outperforms all related art data structures in memory footprint. The data structure, which can be referred to as Compact Fragment-Ion Index Representation (CFIR), is based (at least in part) on the observation that the quantity of unique ion-masses that appear in the fragment-ion data is extremely small compared to the size of data or index. This property in data means that the repeated ion-mass information can be sorted and compressed in an efficient way, significantly reducing the index size. Experimental results confirm that the CFIR data structure consumes at most 50% memory (e.g., at least a 2x improvement) as the best related art data structure while exhibiting the same complexity for index construction and peptide search time. Further, a search speed scalability comparison with increasing index size revealed that the CFIR data structure exhibits optimal performance for up to at least 100% more fragment-ion data as compared to the best related art data structure.

A peak is said to be shared between a pair of mass spectrometry (MS/MS) spectra if both spectra contain a fragment-ion (peak) having m/z (mass divided by charge) within a certain mass difference ($\Delta F$). This tolerance ($\Delta F$) allows conversion of floating point ion m/z's or simply ion-masses to integers by scaling m/z's with a factor (r) where $r \geq 1/\Delta F$. An MS/MS spectrum can therefore be represented as a sparse binary vector over a range of dimensions (0:r:M], where r is the step size and M is the maximum fragment-ion mass. Consider a (sparse) matrix N constructed by stacking all (say, e.g., X) theoretically predicted spectra in the database. Then, the variants of sparse matrix representations, such as Compressed Sparse Row (CSR) and Compressed Sparse Column (CSC), can be used to construct an inverted index by only storing the data for non-zero (NNZ) entries in N. The indexed data typically include information about ion-masses, ion-series, ion-number, and origin spectra IDs for each fragment-ion in N. The shared peak counting is done using the following two index query operations:

rank(N, m): returns the number of occurrences of fragment-ion with m/z (m) in N.

select(N, m, k): returns the position of kth occurrence of fragment-ion with m/z (m) in N.

Therefore, all fragment-ion index structures strive to speed up these two operations. For instance, pFind-Alioth constructs a hash-map where the keys are ion-masses and values are 12-byte entries per indexed fragment-ion to store ion-origin information. MSFragger constructs a sorted-by-ion-mass array containing 8-byte entries per indexed fragment-ion to store ion mass and ion origin information. X! Tandem and Andromeda first filter the search space based on precursor mass and then compute shared peak scores formally scoring the experimental spectra on the fly.

In many embodiments of the subject invention, each theoretical MS/MS spectrum can be represented as an ordered list of numbers where each number represents the (integer) m/z of a predicted fragment-ion in the spectrum. The ions in each generated spectrum $S_i$ are first ordered by their ion-series (b/y) and then ordered by the fragment charge, and finally by their m/z's. However, because the length of a theoretical spectrum varies with the length of parent peptide sequence, all theoretical spectra cannot be stacked together to form the matrix N. Therefore, the database peptide sequences are first grouped by their length and then using all (say: X) theoretical spectra in each group, an instance of matrix $N=[S_1, S_2, \ldots, S_X]$ can be constructed as:

$$N = \begin{bmatrix} i_{11} & \cdots & i_{1k} & \cdots & i_{1n} \\ i_{j1} & \cdots & i_{jk} & \cdots & i_{jn} \\ i_{X1} & \cdots & i_{Xk} & \cdots & i_{Xn} \end{bmatrix}, \quad (1)$$

where $i_{jk}$ corresponds to the m/z of $k^{th}$ fragment-ion in the $j^{th}$ spectrum and $0 \leq i_{jk} \leq (M-1)$. To further simplify the ion indices in N, the ions can be re-enumerated to form a flattened list $T=[i_0, i_1, i_2, \ldots, i_{Xn-1}]$ where original ion-positions can be computed using information about N's dimensions (i.e., dim(N)=(X×n); because the ions are ordered in each spectrum and the spectrum length is fixed per instance of N.

Information in the list T has been observed, and it was found that the number of appearing unique ion m/z's (ion-masses) is extremely small compared to the size of list. Therefore, the ion-mass information, which typically consumes at least 4 bytes (integer) per fragment-ion, can be compressed into a compact representation as follows. A list A containing the indices of ions in T can be defined and given as A=[0, 1, 2, ..., $Xn_{-1}$]. Next, the Stable KeyValue Sort operation can be performed on A using T as a key to yield two arrays: $\Omega$ and $\Lambda$.

$$\Omega, \Lambda = \text{StableKeyValueSort}(T, A). \quad (2)$$

The list $\Lambda$ now contains the locations of sorted fragment-ions in T in the same order as they appear in T, while $\Omega$ is the sorted version of T. Because the T only had a small number of unique ion-masses, its sorted version ($\Omega$) will contain a large number of repeated entries at adjacent indices (i.e., extremely low entropy). Therefore, $\Omega$ can be transformed into a (smaller) list $\Omega'$ by storing only the number of occurrences of each appearing unique ion-mass (i.e., $\Omega'[i]$ ={occs [i]; i∈[0, M−1]}. The new size of $|\Omega'|=M<<X_n=|\Omega|$ where M is the maximum appearing integer mass in T. Next, the occurrences in ST can be successively accumulated to compute an equivalent list $\Omega''$ given as $\Omega''[i]=\Omega''[i-1]+\Omega'[i-1]$. The $\Omega''$ now corresponds to the start positions in $\Lambda$ for each indexed unique ion-mass. The result of the above transformation on T is the two arrays, $\Lambda$ and $\Omega''$, as shown in FIG. 1. The total size of the constructed index is approximately equal to the size of T since $|\Lambda|=Xn=|T|$ whereas $|\Omega''|=M<<|T|$ (~4-bytes per indexed ion). The same transformation can be applied on all instances of N to construct the complete fragment-ion index.

The shared-peaks between an experimental (query) spectrum and the indexed spectra can be counted by first locating occurrences of all query fragment-ion (peak) in T The occurrence locations in T can then be mapped to their origin spectrum IDs (osid) in N followed by counting the number of times a theoretical spectrum's ID (osid) shows up. The algorithm can be translated in terms of rank and select, along with backtrack and update_score in Algorithm 1 (shown below). The two query operations can be computed using the CFIR index representation.

rank(T, mz): can be computed as $\Omega''[mz+1]-\Omega''[mz]$, which is done in O(1) time.

select(T, mz, k): can be located by accessing: $\Lambda[\Omega''[mz]+k]$ which is also done in O(1) time.

The $\Lambda$ elements accessed in select are the ion-positions (pos) in T, which are mapped to their origin-spectrum ID (osid), ion-charge (ichg) and ion-series (iser) information in constant time using the ion ordering information using the backtrack function depicted in Algorithm 2 (shown below). The update score function may have different implementations depending on the employed scoring algorithm.

| Algorithm 1: Shared Peak Counting |
| --- |
| Data: Query fragment mass (qm) |
| Result: Shared Peak Scorecard |
| 1    occs = rank(T, qm): |
| 2    for k in occs do |
| 3        pos = select(T, qm, k): |
| 4        osid, inum, ichg, iser = backtrack(pos); |
| 5        update_score(qm, osid, iser, +1); |

| Algorithm 2: Backtracking Algorithm |
| --- |
| Data: Fragment-Ion position in T (pos) |
| Result: Fragment-Ion information in N |

-continued

| | /* Assuming dim(N) = (X × len) */ |
| --- | --- |
| 1 | osid = ⌊pos/len⌋; |
| 2 | inum = (pos mod (len/2)) + 1; |
| 3 | ichg = ((inum − 1)/(len/$2z_{max}$) + 1); |
| 4 | iser = y_ion; |
| 5 | if (pos mod len)≤(len/2) then |
| 6 |     iser = b_ion; |
| 7 | return osid, inum, ichg, iser; |

Embodiments of the subject invention provide lossless (or nearly lossless) and compact data structure of fragment-ion indexes (can be referred to as CFIR). The data structure can leverage the low entropy in ion-mass information to compress the size of a constructed index. Experimental data (see Examples 1-4 below) show that the fragment-ion data structure outperforms related art fragment-ion indexing structures by at least a factor of 2 in memory consumption while implementing the essential index query functions, rank and select, with no overheads. Because the data structure allows efficient in-core analysis of more fragment-ion data per unit memory, it can be used to optimize existing peptide search algorithms and develop new such algorithms.

Embodiments of the subject invention reduce memory footprint of fragment-ion indexes in database peptide search for mass spectrometry data, and improve the scalability of algorithms. Fragment-ion data can first be transformed for reduction of entropy, and then encoded using a running counter technique to compress the repetitive and redundant information in the index. The data structure outperforms state of the art data structures with a reduction of at least 50% in memory consumption while exhibiting the same time complexity for both index construction and search. The data structure also demonstrates optimal performance for larger data sets using the same amount of resources, compared to state of the art data structures. The data structure can help optimize existing peptide inference algorithms by improving their data index density. It has also applications in development of high-performance computing-based peptide inference algorithms because, in such algorithms, the key to optimal performance is the efficient use of distributed (small) resources.

Embodiments of the subject invention provide a custom data structure that can be used specifically for indexing of fragment-ion data. The data can first be transformed to reduce its entropy, and then it can be encoded to pack the information into a much smaller amount of memory. The data structure does not require any decompression to search the index data, and it provides, without any overheads, all necessary functionality that existing uncompressed structures provide. Publicly available databases were used to evaluate the data structure against related art data structures (see the examples below), and the data structure of embodiments of the subject invention showed more than 2× improvement in memory consumption while showing the same speeds. The data structure also showed improved peptide inference speed performance over growing data size using a given amount of resources.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

A greater understanding of the embodiments of the subject invention and of their many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to the invention.

Example 1

Memory footprint results for a CFIR fragment-ion index of an embodiment of the subject invention were compared against related art indexes—MSFragger, ANN-SoLo, and SpecOMS—for varying data sizes. The index size for MSFragger and CFIR fragment-ion index was varied by increasing the number of modifications added in the protein database. The index size for ANN-SoLo was varied by using spectral libraries of different sizes at the input. The index size for SpecOMS was varied by varying the size of the protein sequence database at its input. All experiments were run on a Windows machine equipped with 20 GB of RAM.

Figure 2:
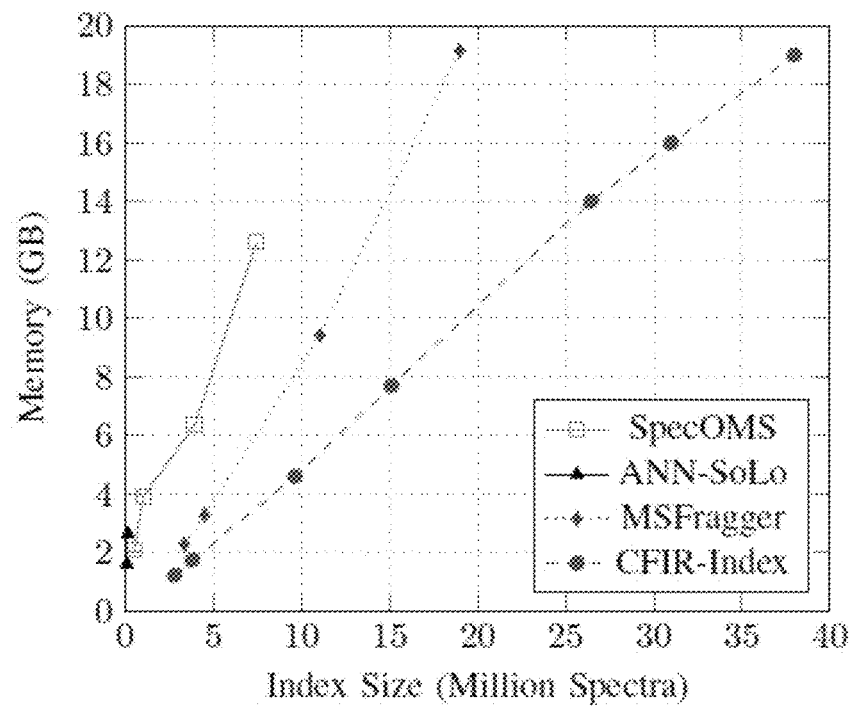
FIG. 2 is a plot of memory (in gigabytes (GB)) versus index size (in millions of spectra) for SpecOMS, ANN-SoLo, MSFragger, and an embodiment of the subject invention (labeled as "CFIR-Index"). The (black) line with the triangle data points is for ANN-SoLo; the (green) line with the square data points is for SpecOMS; the (blue) line with the diamond data points is for MSFragger; and the (red) line with the circle data points is for CFIR-Index.

FIG. 2 is a plot of memory (in GB) versus index size (in millions of spectra) for the tested indexes. The (black) line with the triangle data points is for ANN-SoLo; the (green) line with the square data points is for SpecOMS; the (blue) line with the diamond data points is for MSFragger; and the (red) line with the circle data points is for CFIR-Index. Referring to FIG. 2, the results showed that the CFIR based fragment-ion index consumed at most half the memory as MSFragger fragment-ion index and orders-of-magnitude improvement over ANN-SoLo and SpecOMS index.

Example 2

Figure 3:
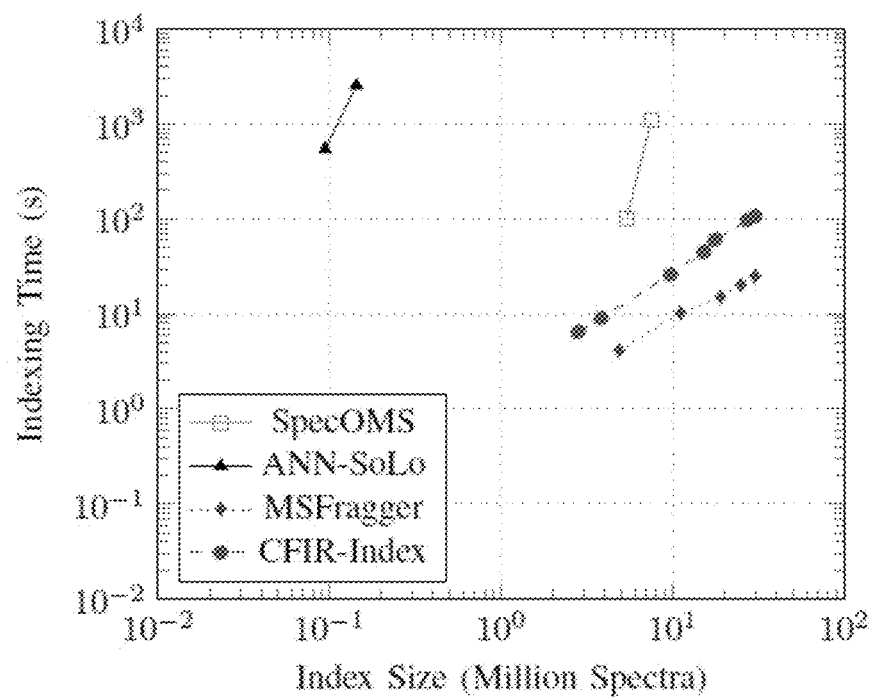
FIG. 3 is a plot of indexing time (in seconds (s)) versus index size (in millions of spectra) for SpecOMS, ANN-SoLo, MSFragger, and an embodiment of the subject invention (labeled as "CFIR-Index"). The (black) line with the triangle data points is for ANN-SoLo; the (green) line with the square data points is for SpecOMS; the (blue) line with the diamond data points is for MSFragger; and the (red) line with the circle data points is for CFIR-Index.

The index construction time results for the indexes used in Example 1 were compared, with varying index size. FIG. 3 is a plot of the indexing time (in seconds (s)) versus index size (in millions of spectra) for the tested indexes. The (black) line with the triangle data points is for ANN-SoLo; the (green) line with the square data points is for SpecOMS; the (blue) line with the diamond data points is for MSFragger; and the (red) line with the circle data points is for CFIR-Index. Referring to FIG. 3, the results show that both MSFragger and CFIR Index have the same time complexity (i.e. O(N log N) whereas ANN-SoLo and SpecOMS exhibit exponential time complexity. Also, because the index construction usually consumes <10% of the total experiment time in normal cases, the slightly slower CFIR index construction time can be ignored in favor of its much better memory efficiency.

Example 3

The peptide search time was analyzed for a CFIR fragment-ion index of an embodiment of the subject invention, using hyperscore (see Kong et al., "Msfragger: ultrafast and comprehensive peptide identification in mass spectrometry-based proteomics," Nature methods, vol. 14, no. 5, p. 513, 2017; which is hereby incorporated by reference herein in its entirety) as an update score for varying MS/MS data and index sizes. The PRIDE Archive data set PXD009072 (305, 000 MS/MS spectra) was searched against the CFIR-index constructed from UniProtKB *Homo sapiens* protein sequence database. The index size was varied by adding post-translational modifications including methionine oxidation, cysteine and lysine gly-gly adducts, and asparagine and glutamine deamidation.

Figure 4:
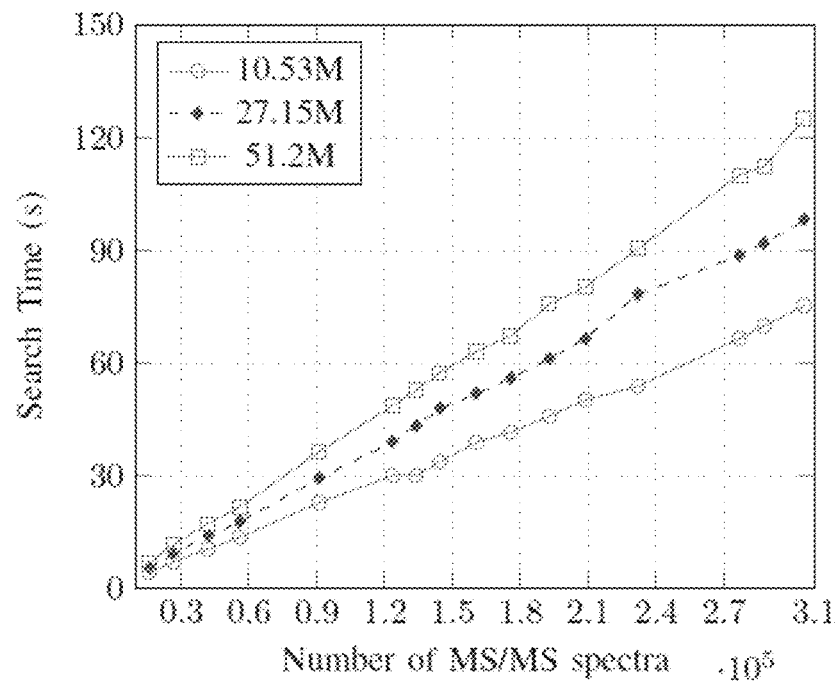
FIG. 4 is a plot of search time (in s) versus number of mass spectrometry (MS/MS) spectra (in $10^5$ spectra) for an embodiment of the subject invention. The (green) line with the circle data points is for 10.53 M; the (blue) line with the diamond data points is for 27.15 M; and the (brown) line with the square data points is for 51.2 M.

FIG. 4 is a plot of search time (in s) versus number of mass spectrometry (MS/MS) spectra (in $10^5$ spectra). The (green) line with the circle data points is for 10.53 M; the (blue) line with the diamond data points is for 27.15 M; and the (brown) line with the square data points is for 51.2 M. Referring to FIG. 4, the results depicted a roughly linear trend with increase in MS/MS data, confirming the constant time complexity for peptide search speed.

Example 4

The peptide search speed scalability was analyzed for a CFIR fragment-ion index of an embodiment of the subject invention and for MSFragger, with increasing fragment-ion data. The experiments were performed on a workstation machine equipped with 8 cores×2 sockets connected to 2 NUMA nodes (16 GB each). The file: FL0320_MSQ805_IBombik_Stimb_6ul.ms2 (17,595 spectra) from the PXD009072 data set was searched against indexes of increasing sizes constructed by successively adding PTMs in the index. The index was allowed to span across NUMA nodes, and the number of parallel cores used in each experiment was fixed to 8 (1 socket).

Figure 5:
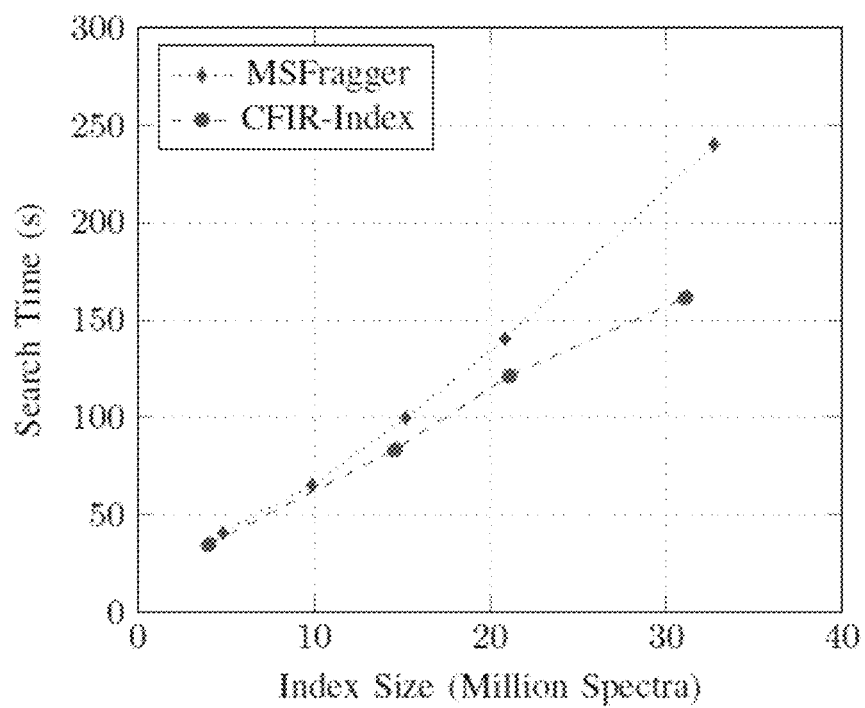
FIG. 5 is a plot of indexing time (in s) versus index size (in millions of spectra) for MSFragger and an embodiment of the subject invention (labeled as "CFIR-Index"). The (blue) line with the diamond data points is for MSFragger; and the (red) line with the circle data points is for CFIR-Index.

FIG. 5 is a plot of indexing time (in s) versus index size (in millions of spectra) for the tested indexes. The (blue) line with the diamond data points is for MSFragger; and the (red) line with the circle data points is for CFIR-Index. Referring to FIG. 5, the results show a performance slowdown for MSFragger beyond index size of 16 million (−12% at 32 million size). The slowdown is caused by non-local memory accesses and page faults (see also Kong et al., supra.). However, the CFIR-index based search shows optimal performance up to index size of 32 million, demonstrating superior performance per compute unit.

The results obtained in Examples 1-4 indicate a reduction memory footprint for the fragment-ion index of embodiments of the subject invention while performing comparably with state of the art indexes in terms of index construction and search speed. The results further show that the CFIR data structure runs at optimal performance for at least twice the index size per memory unit (NUMA node). Modern mass-spectrometry instruments can produce data at astonishing speeds, so peptide search algorithms must also efficiently utilize the available resources on ubiquitous multi-core and multiprocessor architectures for maximum throughput. Embodiments of the subject invention help achieve this.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A system for compressing data to reduce index size, the system comprising:
   a processor; and
   a machine-readable medium in operable communication with the processor and comprising instructions stored thereon that, when executed by the processor, perform the following steps:
   receiving a fragment-ion index comprising the data, the data comprising mass spectrometry data;
   transforming the data to reduce its entropy and give transformed data; and
   encoding the transformed data to reduce an amount of memory used by the transformed data and to give a custom data structure with reduced size compared to the received index,
   the custom data structure being searchable without requiring any decompression prior to searching, such that both individual fragment-ions of the custom data structure and mass spectrometry data of the custom data structure are searchable without requiring any decompression prior to searching,
   the mass spectrometry data comprising mass spectrometry data of one or more peptides, and
   the transforming of the data comprising:
   i) representing each theoretical mass spectrometry spectrum of the data as an ordered list of numbers where each number represents the m/z (mass divided by charge) of a predicted fragment-ion in the spectrum;
   ii) ordering ions in each generated spectrum $S_i$ first by their ion-series (b/y), and then by their fragment charge, and then by their m/z values;
   iii) grouping peptide sequences first by their length and then using all theoretical spectra in each group, where X represents the quantity of theoretical spectra in each group;
   iv) constructing a matrix $N=[S_1, S_2, \ldots, S_X]$ as $$N = \begin{bmatrix} i_{11} & .. & i_{1k} & .. & i_{1n} \\ i_{j1} & .. & i_{jk} & .. & i_{jn} \\ i_{X1} & .. & i_{Xk} & .. & i_{Xn} \end{bmatrix},$$

where $i_{jk}$ corresponds to the m/z of $k^{th}$ fragment-ion in the $j^{th}$ spectrum, $0 < i_{jk} \leq (M-1)$, and M is maximum fragment-ion mass;

v) re-enumerating the ions to form a flattened list $T=[i_0, i_1, i_2, \ldots, i_{Xn-1}]$;

vi) defining a list A containing indices of ions in T, where $A=[0, 1, 2, \ldots, Xn_{-1}]$, where a dimension of N is given as $\dim(N)=(X \times n)$; and vii) performing a Stable KeyValue Sort operation on A using T as a key to yield the transformed data in array $\Omega$ and array $\Lambda$ ($\Omega$, $\Lambda$=StableKeyValueSort(T,A)).

2. The system according to claim 1, the encoding of the transformed data comprising:

viii) transforming $\Omega$ into a list $\Omega'$ by storing only a number of occurrences of each appearing unique ion-mass ($\Omega'[i]=\{occs\ [i];\ i \in [0, M-1]\}$), where $|\Omega'|=M<<X_n=|\Omega|$.

3. The system according to claim 2, the encoding of the transformed data further comprising:

ix) computing an equivalent list $\Omega''$ given as $\Omega''[i]=\Omega''[i-1]+\Omega'[i-1]$ by successively accumulating occurrences in $\Omega'$, where $\Omega''$ corresponds to start positions in A for each indexed unique ion-mass.

4. The system according to claim 2, the transforming and encoding further comprising performing steps v)-viii) on all instances of N to construct the complete fragment-ion index.

5. The system according to claim 1, the transforming of the data further comprising performing steps v)-vii) on all instances of N.

6. The system according to claim 1, the encoding of the transformed data comprising using a running counter technique to compress repetitive and redundant information in the transformed data.

7. The system according to claim 1, the encoding of the transformed data comprising using a running counter technique to compress repetitive and redundant information in the transformed data.

8. A method for compressing data to reduce index size, the method comprising:
   receiving a fragment-ion index comprising the data, the data comprising mass spectrometry data;
   transforming, by a processor, the data to reduce its entropy and give transformed data, and
   encoding, by the processor, the transformed data to reduce an amount of memory used by the transformed data and to give a custom data structure with reduced size compared to the received index,
   the custom data structure being searchable without requiring any decompression prior to searching, such that both individual fragment-ions of the custom data structure and mass spectrometry data of the custom data structure are searchable without requiring any decompression prior to searching,
   the mass spectrometry data comprising mass spectrometry data of one or more peptides, and
   the transforming of the data comprising:
   i) representing each theoretical mass spectrometry spectrum of the data as an ordered list of numbers where each number represents the m/z (mass divided by charge) of a predicted fragment-ion in the spectrum;
   ii) ordering ions in each generated spectrum S; first by their ion-series (b/y), and then by their fragment charge, and then by their m/z values;
   iii) grouping peptide sequences first by their length and then using all theoretical spectra in each group, where X represents the quantity of theoretical spectra in each group;
   iv) constructing a matrix $N=[S_1, S_2, \ldots, S_X]$ as $$N = \begin{bmatrix} i_{11} & .. & i_{1k} & .. & i_{1n} \\ i_{j1} & .. & i_{jk} & .. & i_{jn} \\ i_{X1} & .. & i_{Xk} & .. & i_{Xn} \end{bmatrix},$$

where $i_{jk}$ corresponds to the m/z of $k^{th}$ fragment-ion in the $j^{th}$ spectrum, $0 < i_{jk} \leq (M-1)$, and M is maximum fragment-ion mass;

v) re-enumerating the ions to form a flattened list $T = [i_0, i_1, i_2, \ldots, i_{Xn-1}]$;

vi) defining a list A containing indices of ions in T, where $A = [0, 1, 2, \ldots, Xn_{-1}]$, where a dimension of N is given as $\dim(N) = (X \times n)$; and vii) performing a Stable KeyValue Sort operation on A using T as a key to yield the transformed data in array $\Omega$ and array $\Lambda$ ($\Omega, \Lambda = \text{StableKeyValueSort}(T,A)$).

9. The method according to claim 8, the encoding of the transformed data comprising:

viii) transforming $\Omega$ into a list $\Omega'$ by storing only a number of occurrences of each appearing unique ion-mass ($\Omega'[i] = \{occs\ [i];\ i \in [0, M-1]\}$), where $|\Omega'| = M << X_n = |\Omega|$.

10. The method according to claim 9, the encoding of the transformed data further comprising:

ix) computing an equivalent list $\Omega''$ given as $\Omega''[i] = \Omega''[i-1] + \Omega'[i-1]$ by successively accumulating occurrences in $\Omega'$, where $\Omega''$ corresponds to start positions in $\Lambda$ for each indexed unique ion-mass.

11. The method according to claim 9, the transforming and encoding further comprising performing steps v)-viii) on all instances of N to construct the complete fragment-ion index.

12. The method according to claim 8, the transforming of the data further comprising performing steps v)-vii) on all instances of N.

13. The method according to claim 8, the encoding of the transformed data comprising using a running counter technique to compress repetitive and redundant information in the transformed data.

14. A system for compressing data to reduce index size, the system comprising:
a processor; and
a machine-readable medium in operable communication with the processor and comprising instructions stored thereon that, when executed by the processor, perform the following steps:
receiving an index comprising the data;
transforming the data to reduce its entropy and give transformed data; and
encoding the transformed data to reduce an amount of memory used by the transformed data and to give a custom data structure with reduced size compared to the received index,
the custom data structure being searchable without requiring any decompression prior to searching,
the index being a fragment-ion index and the data comprising mass spectrometry data,
the mass spectrometry data comprising mass spectrometry data of one or more peptides,
the transforming of the data comprising:
i) representing each theoretical mass spectrometry spectrum of the data as an ordered list of numbers where each number represents the m/z (mass divided by charge) of a predicted fragment-ion in the spectrum;
ii) ordering ions in each generated spectrum $S_i$ first by their ion-series (b/y), and then by their fragment charge, and then by their m/z values;
iii) grouping peptide sequences first by their length and then using all theoretical spectra in each group, where X represents the quantity of theoretical spectra in each group;
iv) constructing a matrix $N = [S_1, S_2, \ldots, S_X]$ as $$N = \begin{bmatrix} i_{11} & .. & i_{1k} & .. & i_{1n} \\ i_{j1} & .. & i_{jk} & .. & i_{jn} \\ i_{X1} & .. & i_{Xk} & .. & i_{Xn} \end{bmatrix},$$

where $i_{jk}$ corresponds to the m/z of $k^{th}$ fragment-ion in the $j^{th}$ spectrum, $0 < i_{jk} \leq (M-1)$, and M is maximum fragment-ion mass;

v) re-enumerating the ions to form a flattened list $T = [i_0, i_1, i_2, \ldots, i_{Xn-1}]$;

vi) defining a list A containing indices of ions in T, where $A = [0, 1, 2, \ldots, Xn_{-1}]$, where a dimension of N is given as $\dim(N) = (X \times n)$; and vii) performing a Stable KeyValue Sort operation on A using T as a key to yield the transformed data in array $\Omega$ and array $\Lambda$ ($\Omega, \Lambda = \text{StableKeyValueSort}(T,A)$), the encoding of the transformed data comprising:

viii) transforming $\Omega$ into a list $\Omega'$ by storing only a number of occurrences of each appearing unique ion-mass ($\Omega'[i] = \{occs\ [i];\ i \in [0, M-1]\}$), where $|\Omega'| = M << X_n = |\Omega|$; and ix) computing an equivalent list $\Omega''$ given as $\Omega''[i] = \Omega''[i-1] + \Omega'[i-1]$ by successively accumulating occurrences in $\Omega'$, where $\Omega''$ corresponds to start positions in $\Lambda$ for each indexed unique ion-mass, and the transforming and encoding further comprising performing steps v)-ix) on all instances of N to construct the complete fragment-ion index.

\* \* \* \* \*